United States Patent [19]

Guenther et al.

[11] Patent Number: 4,823,369

[45] Date of Patent: Apr. 18, 1989

[54] DENTAL X-RAY DIAGNOSTICS INSTALLATION FOR PRODUCING PANORAMA SLICE EXPOSURES OF THE JAW OF A PATIENT

[75] Inventors: Werner Guenther; Manfred Muether; Erich Heubeck, all of Bensheim; Michael Doebert, Lorsch; Leonhard Werner, Hemsbach, all of Fed. Rep. of Germany

[73] Assignee: Siemens Aktiengesellschaft, Berlin and Munich, Fed. Rep. of Germany

[21] Appl. No.: 140,123

[22] Filed: Dec. 31, 1987

[30] Foreign Application Priority Data

Feb. 16, 1987 [DE] Fed. Rep. of Germany ....... 3704857

[51] Int. Cl.⁴ ............................................... A61B 6/00
[52] U.S. Cl. ......................................... 378/22; 378/39; 378/21
[58] Field of Search ................................... 378/38–40, 378/21, 22

[56] References Cited

U.S. PATENT DOCUMENTS

| | | | |
|---|---|---|---|
| 4,188,537 | 2/1980 | Franke | 378/39 |
| 4,239,971 | 12/1980 | Cushman | 378/39 |
| 4,298,800 | 11/1981 | Goldman | 378/19 |
| 4,383,327 | 5/1983 | Kruger | 378/19 |
| 4,492,869 | 1/1985 | Suzuki et al. | 250/367 |

FOREIGN PATENT DOCUMENTS 0138625 4/1985 European Pat. Off. .

OTHER PUBLICATIONS

"Direct Soft X-Ray Response of a Charge-Coupled Image Sensor," Koppel, Rev. Sci. Instrum., vol. 48, No. 6, Jun. 1977, pp. 669–672.

Primary Examiner—Craig E. Church
Assistant Examiner—John C. Freeman
Attorney, Agent, or Firm—Hill, Van Santen, Steadman & Simpson

[57] ABSTRACT

A dental x-ray diagnostics installation has a rotary unit carrying an x-ray source and a radiation detector disposed behind a secondary diaphragm, the rotary unit rotating around the jaw of a patient to produce panorama tomograph exposures of the patient's jaw. The radiation detector generates electrical signals proportional to the incident radiation intensity. To simplify signal processing, the detector is formed of one or more semiconductor detectors having a scintillation layer which corresponds to the size of the opening in the secondary diaphragm. The voltages acquired by the detector are converted to digital form, and stored in an image memory. A computer calculates a total image from the signals supplied by the detector, and stored in the memory, during a complete exposure. The signals from the image memory are combined to generate a tomogram of a desired slice of the patient's jaw.

8 Claims, 1 Drawing Sheet

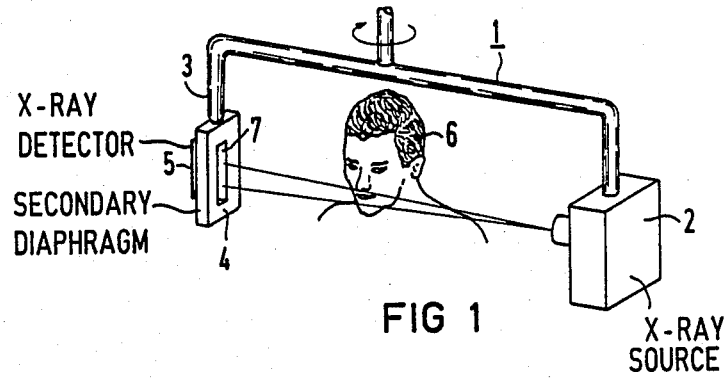
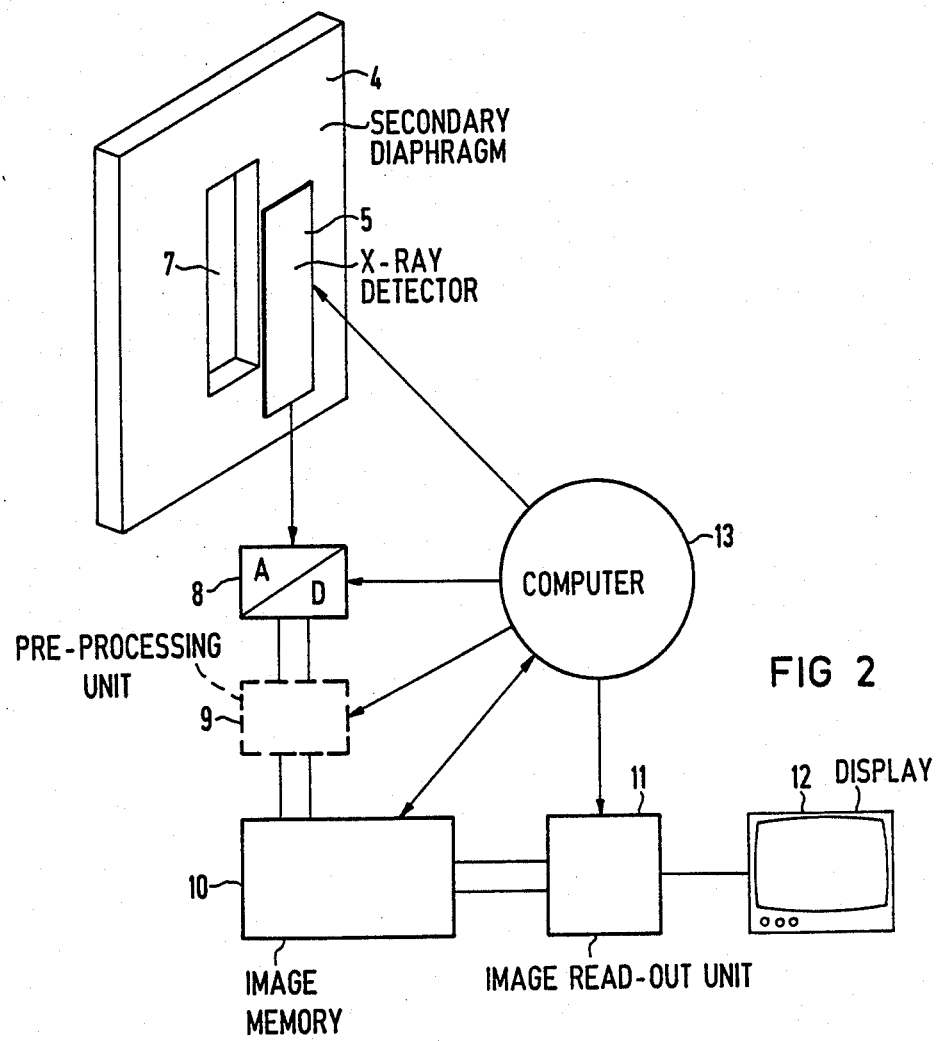

DENTAL X-RAY DIAGNOSTICS INSTALLATION FOR PRODUCING PANORAMA SLICE EXPOSURES OF THE JAW OF A PATIENT

BACKGROUND OF THE INVENTION

1. Field of the Invention

The present invention is directed to an x-ray diagnostics installation for dental examinations, and in particular to such an installation for producing panorama tomograms of the jaw of a patient.

2. Related Application

The present application is related to another application entitled "Dental X-Ray Diagnostics Installation For Producing Panorama Slice Exposures of the Jaw of a Patient" (Dr. Joachim Pfeiffer, Werner Guenther, Manfred Muether and Erich Heubeck) filed, simultaneously herewith and having Ser. No. 150,379.

3. Description of the Prior Art

A dental x-ray diagnostics installation is described in German Patent No. 26 46 638, corresponding to U.S. Pat. No. 4,188,537. This installation includes a unit which is rotatable about a vertical axis which has an x-ray source and a secondary diaphragm, with a detector disposed behind the diaphragm, mounted thereon. The carrier is rotated about the head of a patient as the patient is exposed to x-radiation, and the detector generates electrical signals proportional to the intensity of the radiation incident thereon. The electrical signals are supplied to an analog-to-digital converter, with the resulting digital signals being entered and stored in an image memory. A computer uses the stored data to calculate a complete image of the patient's jaw obtained during a full exposure, and the image is visually represented by an image reproduction means.

In the above-described known system, the panorama x-ray exposure can be electronically recorded and stored, instead of being recorded and stored in the conventional manner on x-ray film. This permits the image to be reproduced on a television monitor.

SUMMARY OF THE INVENTION

It is an object of the present invention to provide a dental x-ray diagnostics installation for producing panorama tomograms of the jaw of a patient wherein image pick-up and processing of the signals are simplified.

The above object is achieved in accordance with the principles of the present invention in an x-ray diagnostics installation having a secondary radiation diaphragm with an opening therein, with one or more individual detectors disposed behind the diaphragm corresponding to the size of the opening therein. The detectors preferably consist of amorphous silicon (aSi:H), and have a relatively short read-out time of, for example, less than 5 ms for each image through the opening.

A pre-processing unit may be provided which adds only signals from a few adjacent diaphragm images as a function of time, rather than adding all of the signals, so that a tomograph of a desired slice (i.e., a desired depth) is generated. If, however, an image memory is provided with a sufficiently large memory capacity, and if the physical size and cost of such a memory are justifiable, the pre-processing unit can be eliminated.

DESCRIPTION OF THE DRAWINGS

FIG. 1 is a perspective view of an x-ray diagnostics installation constructed in accordance with the principles of the present invention.

FIG. 2 is a schematic block diagram of signal processing components in the x-ray diagnostics installation constructed in accordance with the principles of the present invention.

DESCRIPTION OF THE PREFERRED EMBODIMENTS

The x-ray diagnostics installation shown in FIG. 1, constructed in accordance with the principles of the present invention, includes a rotary unit generally referenced at 1, consisting of an x-ray source 2 and a secondary diaphragm 4, with a detector arrangement 5 attached thereto, mounted at opposite ends of a carrier 3. The rotary unit 1 can be rotated around the head of a patient 6 in a known manner, as indicated by the arrow. Adjustment and control devices for generating a panorama tomogram of the jaw of the patient 6 using such a unit are known to those skilled in the art, and need not be further described. It need only be noted that the head of the patient 6 is fixed in position with a mount during an exposure, and the rotary unit 1 moves with a defined speed around the patient 6 given a prescribed exposure time. This movement is undertaken such that the x-rays emitted by the x-ray source 2 are always incident on the jaw of the patient 6 at substantially a right angle, and a substantially constant distance between the jaw and the detector arrangement 5 is maintained.

As also shown in FIG. 1, and shown enlarged in FIG. 2, the secondary diaphragm 4 has a slot or opening 7 therein having a size, for example, of 5×125 mm. The detector arrangement 5 may consist of a single semiconductor image recorder having a scintillation layer applied thereto. The scintillation layer may be coupled to the semiconductor portion of the detector arrangement 5 either directly, or through a fiber-optic plate. The semiconductor image recorder has at least the dimensions of the secondary diaphragm opening 7. This semiconductor portion consists of a photodiode array of amorphous silicon. To maintain a meaningful resolution, the pixel size is preferably less than 0.3 mm×0.3 mm. To maintain blurring as low as possible, the detector has a read-out time of less than 5 ms, corresponding to a read-out time of less than one microsecond per pixel.

The output of the detector arrangement 5 is supplied to an analog-to-digital converter 8, which is followed by a digital image processing system including a pre-processing unit 9, an image memory 10, an image read-out unit 11, a display 12 and a computer 13.

Image information in the form of voltage signals which are proportional to the x-ray-intensity for a pixel of the detector arrangement 5 are supplied at the output of the detector arrangement 5. These voltages are converted to digital signals in the converter 8. These digital values can then either be directly entered and stored in the image memory 10, or can be entered and stored in the image memory 10 after pre-processing in the unit 9. The computer 13 provides control (read-out) instructions required for this purpose.

Direct entry of signals from the analog-to-digital converter 8 into the image memory 10 is preferable if the image memory 10 has a sufficiently large memory capacity, which can be justified given the constraints of cost and physical size. If direct entry is undertaken, the data are stored only during the rotation of the rotary unit 1 which is necessary to complete an exposure, and after the conclusion of this exposure the data are processed, i.e., are added to generate a tomogram of the desired slice of the patient's jaw. Even though a relatively large amount of data must be processed for this purpose, this method has the advantage that a subsequent visual representation of a plurality of different slices is possible.

If, however, it is not economically justifiable to provide an image memory 10 having such a large memory capacity, the pre-processing 9 may be interposed between the converter 8 and the image memory 10, as indicated with dashed lines in FIG. 2. The pre-processing unit 9 includes an intermediate memory and a signal processor, by means of which the digital data from the converter 8 are added as a function of time based on a control instruction from the computer 13. This addition is undertaken to generate a tomogram of the desired slice of the patient's jaw. The processed data are subsequently forwarded to the image memory 10. An image memory 10 having a lower memory capacity can thus be used if the pre-processing unit 9 is present. If the preprocessing unit 9 is used, however, the slice or tomograph position (i.e., depth) is fixed, so that the slice position can not be varied within certain limits, as would be possible without the pre-processing unit 9 wherein the image data are not combined to form a tomogram until after a complete exposure.

A compromise solution is possible, however, wherein a plurality of adjacent image columns (i.e., data sets corresponding to successive positions of the secondary diaphram 4, and thus of the opening 7 therein) are added as a function of time before storing this data, and the subsequent addition of these sum columns to form an image column is not undertaken until after storing the data. Using this method, the pre-processing unit 9 is not required to add all of the data, but only the data for a few adjacent columns. The data for these few columns are added as a function of time under the control of the computer 13, and are then forwarded to the image memory 10.

A full description of the creation of an image in accordance with the principles of the present invention is as follows. Upon activation of the x-ray source 2, and rotation of the rotary unit 1, electronic signals are generated by the detector arrangement 5 at every angular degree, these signals being proportional to the radiation intensity of the radiation attenuated by the patient's head, and limited by the opening 7 in the secondary diaphragm 4.

The radiation energy proceeding through the opening 7 changes constantly as the x-ray source 2 moves slowly around the head of the patient 6. Denser tissue, such as bones and teeth, absorb a greater quantity of x-radiation than soft tissue, so that a correspondingly reduced amount of -radiation reaches the detector arrangement 5 at those locations, and a less dense image of that tissue results. If the radiation at any given time were to be converted into an image, this image would have essentially the same dimensions as the opening 7, and the radiation intensity at every point of the image would correspond to the density of the subject along the direction of propagation of the x-radiation at this point. Such column patterns in the form of digital values are continuously stored and added as a function of time with the assistance of the computer 13, and are then electronically combined to form a complete image. The addition as a function of time is undertaken as though, using conventional methods, x-ray film in a film cassette was being moved along behind the opening 7 at a film speed v. The addition is then undertaken according to the following relationship:

$$S_{ni} = \sum_{m=1}^{M} \delta_{mi}(t - ma/v)$$

wherein $i = 1 \ldots i$ and is the line number in the completed image, with $i_{max}$ being the number of lines in the completed image; $n = 1 \ldots n_{max}$, with n being the column number in the completed image and $n_{max}$ being the number of columns in the completed image; $S_{ni}$ is the value of the pixel in the $i^{th}$ line and nth column of the completed image; M is the number of columns in the image recorder (i.e., in the detector arrangement 5); $\delta_{mi}(t)$ is the value of the pixel in the $m^{th}$ column and the $i^{th}$ line of the image recorder at time t; and a is the pixel size.

As is known, the speed with which the film is conducted past the opening in the secondary diaphragm in conventional panorama methods can be varied to select a desired position and shape of the tomogram of the subject. In the method disclosed herein, the same selection is made by undertaking addition of the data using different time functions, which correspond to varying the film speed in conventional methods. Computational techniques for this purpose are described in the aforementioned related application.

Although modifications and changes may be suggested by those skilled in the art it is the intention of the inventors to embody within the patent warranted hereon all changes and modifications as reasonably and properly come within the scope of their contribution to the art.

We claim as our invention:

1. A dental x-ray diagnostics installation for producing panorama tomograms of the jaw of a patient comprising:
   an x-ray source;
   a secondary diaphragm having an opening therein;
   an x-ray detector disposed behind said opening of said secondary diaphragm and having a size coincident with said opening, said x-ray detector consisting of at least one semiconductor substrate with a scintillation layer thereon and generating electrical signals corresponding to x-radiation incident on said x-ray detector;
   means for rotating said x-ray source, said secondary diaphragm and said x-ray detector around the jaw of said patient with the jaw disposed between the x-ray source and the detector so that x-radiation attenuated by the jaw is incident on said detector;
   means connected to said x-ray detector for selectively adding less than all of the signals from said x-ray detector as a function of time to generate successive sets of added signals;
   means for storing said sets of added signals; and
   means for adding said sets of added signals as a function of time to generate a tomogram of a selected slice of said jaw.

2. An x-ray diagnostics installation as claimed in claim 1, wherein said semiconductor substrate has a pixel size of less than or equal to 0.5×0.5 mm.

3. An x-ray diagnostics installation as claimed in claim 1, wherein said semiconductor substrate is formed from amorphous silicon.

4. An x-ray diagnostics installation as claimed in claim 1, wherein said x-ray detector consists of a single detector having the same size opening in said secondary diaphragm.

5. A dental x-ray diagnostics installation for producing panorama tomograms of the jaw of a patient comprising:
   an x-ray source;
   a secondary diaphragm having an opening therein;
   a carrier for carrying said x-ray source and said secondary diaphragm;
   an x-ray detector disposed behind said opening of said secondary diaphragm and having a size coincident with said opening, said x-ray detector consisting of at least one semiconductor substrate with a scintillation layer thereon and generating electrical signals corresponding to x-radiation incident on said x-ray detector;
   means for rotating said x-ray source, said secondary diaphragm and said x-ray detector around the jaw of said patient with the jaw disposed between the x-ray source and the detector so that x-radiation attenuated by the jaw is incident on said detector;
   a digital image processing system including an analog-to-digital converter, converting the signals coming from the x-ray detector to digital signals;
   pre-processing means for selectively adding less than all of the signals from said x-ray detector, and converted into digital signals, as a function of time to generate successive sets of added digital signals;
   means for storing said sets of added digital signals; and
   an image read-out-unit, a display and a computer, said computer controlling said x-ray detector, said storage means and said image read-out-unit, and adding said sets of added digital signals as a function of time to generate a tomogram of a selected slice of said jaw.

6. An x-ray diagnostics installation as claimed is claim 5, wherein said semiconductor substrate is formed from amorphous silicon and consists of a single detector having the same size as said opening in said secondary diaphragm.

7. A method for operating an x-ray diagnostics installation for producing panorama tomograms of the jaw of a patient comprising the steps of:
   irradiating the jaw of said patient with x-radiation from an x-ray source;
   receiving x-radiation attenuated by the jaw of said patient on an x-ray detector disposed behind a secondary diaphragm and consisting of at least one semiconductor substrate with a scintillation layer thereon;
   generating electronic signals from said x-ray detector corresponding to the attenuated x-radiation incident on said x-ray detector;
   rotating said x-ray source, said secondary diaphragm and said x-ray detector around the jaw of said patient;
   adding less than all of said signals from said x-ray detector as a function of time to generate a plurality of sets of added data;
   storing said sets of added data; and
   adding said sets of added data as a function of time to generate a tomograph of a selected slice of said jaw.

8. A dental x-ray diagnostics installation for producing panorama tomographs of the jaw of a patient comprising:
   an x-ray source;
   a secondary diaphragm having an opening therein;
   a carrier for carrying said x-ray source and said secondary diaphragm;
   a single x-ray detector disposed behind said opening of said secondary diaphragm and having a size coincident with said opening, said x-ray detector consisting of at least one semiconductor substrate with a scintillation layer thereon and generating electrical signals corresponding to x-radiation incident on said x-ray detector;
   means for rotating said x-ray source, said secondary diaphragm and said x-ray detector around the jaw of said patient with the jaw disposed between the x-ray source and the detector so that x-radiation attenuated by the jaw is incident on said detector;
   a digital image processing system including an analog-to-digital converter for converting the signals coming from the x-ray detector to digital signals;
   means for storing data corresponding to said digital signals from the detector; and
   an image read-out unit, a display and a computer, said computer controlling the x-ray detector, said means for storing and said image read-out unit and adding said data as a function of time to generate a tomogram of a selected slice of said jaw.

* * * * *